(12) United States Patent
Weickmann

(10) Patent No.: US 6,998,389 B2
(45) Date of Patent: Feb. 14, 2006

(54) PHARMACEUTICAL COMPOSITION COMPRISED OF SPIDER VENOMS, THE PRODUCTION THEREOF, AND ITS USE FOR TREATING TUMOR DISEASES

(75) Inventor: Dirk Weickmann, Munich (DE)

(73) Assignee: Toximed GmbH, (DE)

( * ) Notice: Subject to any disclaimer, the term of this patent is extended or adjusted under 35 U.S.C. 154(b) by 490 days.

(21) Appl. No.: 10/168,068

(22) PCT Filed: Dec. 18, 2000

(86) PCT No.: PCT/EP00/12902

§ 371 (c)(1),
(2), (4) Date: Oct. 7, 2002

(87) PCT Pub. No.: WO01/43754

PCT Pub. Date: Jun. 21, 2001

(65) Prior Publication Data

US 2003/0175261 A1 Sep. 18, 2003

(30) Foreign Application Priority Data

Dec. 17, 1999 (DE) ............................. 199 61 141

(51) Int. Cl.
*A61K 38/02* (2006.01)
*A61K 38/46* (2006.01)
*A61K 3835/64* (2006.01)

(52) U.S. Cl. ........................... 514/21; 514/2; 424/538; 424/94.62; 424/94.6

(58) Field of Classification Search ................. 514/2, 514/21; 424/538, 94.62, 94.6
See application file for complete search history.

(56) References Cited

U.S. PATENT DOCUMENTS

| 4,877,741 A | 10/1989 | Babcock et al. |
| 4,925,664 A | 5/1990 | Jackson et al. |
| 5,196,193 A * | 3/1993 | Carroll .................. 424/172.1 |

FOREIGN PATENT DOCUMENTS

WO WO 95/19989 7/1995

OTHER PUBLICATIONS

Bettini, Sergio (ed.), *Arthropod Venoms*, pp. 251-260. Handbuch der experimentellen Pharmakologie (*Handbook of Experimental Pharmacology*), vol. 48 (1978).

Burda, R. et al. "Zellzerstörende Giftkomponenten von Spinnen der Gattung Sicarius bei der Therapie von Tumorkrankungen (Cell Destructive Toxic Components of Spiders of the Genus Sicarius for Tumor Therapy)." *Ärztezeitschrift für Naturheilverfahren* 41, 3, pp. 172-177 (2000).

Geren, Collis R. et al. "Isolation and Characterization of Toxins from Brown Recluse Spider Venom (*Loxosceles reclusa*)." *Archives of Biochemistry and Biophysics* 174, pp. 90-99 (1976).

Kurpiewski, Gretchen et al. "Platelet Aggregation and Sphingomyellnase D Activity of a Purified Toxin from the Venom of Loxosceles Reclusa." *Toxicology*, vol. 96, pp. 166-167 (1982).

Merchant, Michael et al. "Observation of Phospholipase Activity in the Venom of the Brown Recluse Spider (*Loxosceles Reclusa*) by Phosphorous-31 NMR." *FASEB Journal*, vol. 9, No. 6, p. A1313. Meeting Info: Annual Meeting of the American Society for Biochemistry and Molecular Biology, San Francisco, California, May 21-25, 1995.

Suárez, Gerardo et al. "Effect Extracts of the Venom Gland of the Recluse Spider, *Loxosceles Laela*, on Human Cells in Culture." *Toxicon*, vol. 14, pp. 335-337 (1976).

Wright, R.P. et al. "Hyaluronidase and Esterase Activities of the Venom of the Poisonous Brown Recluse Spider." *Archives of Biochemistry and Biophysics* 159, pp. 415-426 (1973).

* cited by examiner

*Primary Examiner*—Jean C. Witz
(74) *Attorney, Agent, or Firm*—M. Henry Heines; Townsend and Townsend and Crew, LLP

(57) ABSTRACT

The present invention describes pharmaceutically effective substances from the poison of spiders of the family of Sicariidae as well as their preparation and their use in medicine.

22 Claims, 6 Drawing Sheets

PHARMACEUTICAL COMPOSITION COMPRISED OF SPIDER VENOMS, THE PRODUCTION THEREOF, AND ITS USE FOR TREATING TUMOR DISEASES

The present invention relates to pharmaceutical compositions containing at least a peptide toxin as well as at least a substance having an antagonistic effect thereon, and/or a penetrant in a pharmaceutically effective amount wherein at least the peptide toxin and optionally the substance having an antagonist effect, and/or the penetrant is derived from the poison of spiders of the family of Sicariidae, as well as to the preparation and the use of the pharmaceutical compositions.

PRIOR ART

In the case of locally manifested tumors, currently, resecting the tumor as completely as possible is the most common form of therapy. Prior to the operation, the tumor is localized using imaging methods and then manually resected by means of an opening intervention. During this, it is impossible to prevent a contact between the operation area and air. It is known from the literature (Stegner H.-E. (1986): Histopathologie der Mammatumoren. Enke Verlag, Stuttgart; Garbe C., Dummer R., Kaufmann R. and Tielgen W. (1997): Dermatologische Onkologie. Springer Verlag, Berlin (see also errata)) that because of the contact with air a metastasis rate of the primary tumor of 93% can be expected.

Other forms of therapy for the treatment of tumors are chemotherapy, irradiation, antibody therapy, cytokine treatment, hyperthermic treatment, or oxygen therapy.

Generally, cell toxins are employed in the chemotherapy of tumors to treat tumors spread throughout the entire body and tumor cells remaining after surgical resection of local tumors (Römpp, Chemielexikon, $9^{th}$ edition, vol. 1, 1989, p. 680). Substances used in chemotherapy include for example alkylating substances, anti-metabolites, alkaloids, antibiotics, and hormones (Römpp Lexikon, Biotechnologie und Gentechnik, $2^{nd}$ edition, 1999, p. 153). Known as alkylating compounds are for example cisplatin, nitroso urea compounds, or thiotepa. Furthermore, folic acid antagonists, e.g. aminopterine, pyrimidine analogs such as fluorouracil are employed. As antibiotics having an inhibitory effect on DNA-dependent RNA polymerase there may be mentioned bleomycin, doxorubicine, or mitomycin C. Also enzymes such as L-asparaginase have been used in chemotherapy.

The disadvantages of chemotherapy are that it is difficult to use the chemotherapeutics in a site-specific manner and that these cytostatics are extraordinarily severe cell toxins which in addition to the tumor tissue also damage to a great extent healthy tissues including liver and kidney cells. Because of the systemic distribution of the cytostatics it is difficult to judge the side effects arising such as alopecia, vertigo, vomiting, gastro-intestinal bleeding, disturbed circulation etc. (Deutsches Krebsforschungszentrum DKFZ Heidelberg—Focus 19/1995). These numerous, dangerous and undesirable side effects may be explained mainly by an inhibition of the regeneration of quickly proliferating tissues and particularly affect the hematopoietic system, the mucosal and gonadal epithelia, as well as the skin and skin appendages. Among the life-threatening complications infections are the most important, followed by bleeding (Pschyrembel—Klinisches Wörterbuch, $256^{th}$ edition, 1990, page 1866).

Irradiation is carried out by means of ionizing radiation wherein generally electron, gamma, neutron, or X-ray beams are used (Zetkin/Schaldach: Lexikon der Medizin, $16^{th}$ edition, 1999, page 1922/1923, Ullstein Medical). Similar to chemotherapy, the disadvantage of irradiation is the impossibility to achieve a spatial restriction. Because of the intensity of the radiation also healthy cells and particularly the DNA are severely damaged. Since cancer cells generally divide faster than normal cells, under typical circumstances the cancer cells are the first to be destroyed in radiotherapy. However, there is the risk developing a radiation ulcer (Pschyrembel—Klinisches Wörterbuch 256, edition 1990, page 1602).

Therefore, it is an object of the present invention to provide improved means and methods useful in tumor therapy and/or as an accompanying therapy e.g. in surgical/operative treatment of tumor diseases and which avoid the above-mentioned disadvantages of the prior art.

According to the present invention, this has been achieved by a pharmaceutical composition containing in a pharmaceutically effective amount:
a) at least one peptide toxin as well as
b) at least one substance having an antagonistic effect thereon and/or at least a penetrant
wherein at least the peptide toxin is derived from the poison of spiders of the family of Sicariidae and optionally the substance having an antagonistic effect thereon and/or the penetrant is derived from the poison of spiders of the family of Sicariidae.

Moreover, advantageously one or more additional substances from the poison of spiders of the family of Sicariidae may be contained in the pharmaceutical compositions according to the present invention. In another embodiment, there may preferably contained additional substances derived from other poison-containing organisms.

Among the spiders of the family of Sicariidae, the genera *Sicarius, Loxosceles, Scytodes* and *Drymusa* are preferred.

Pharmaceutical compositions are preferred in which the peptide toxin as well as the substance having an antagonistic effect and/or the penetrant are derived from the poison of the spider species *Sicarius, Loxosceles, Scytodes*, and *Drymusa*.

Further preferred are pharmaceutical compositions in which the peptide toxin as well as the substance having an antagonistic effect and/or the penetrant are derived from the poison of the *Sicarius* spider species *Sicarius oweni, Sicarius testaceus, Sicarius hahni*, and *Sicarius albospinosus*, the *Loxosceles* spider species *Loxosceles reclusa, Loxosceles rufipes*, and *Loxosceles laeta*, and/or the *Scytodes* spider species *Scytodes thoracica, Scytodes rufa*, and *Scytodes longipes*. This has the advantage that thereby the natural interplay of peptide toxins and substances having an antagonistic effect thereon of a single organism may be utilized.

According to the present invention, the substance having an antagonistic effect and/or the penetrant, however, may also be derived from a different organism or may be prepared synthetically of by genetic engineering, or an additional peptide toxin derived from another organism may be included. For example, the snake poison captopril may be included as another peptide toxin, or the substance having an antagonistic effect may be a hyaluronidase derived from cobra poisons.

According to the present invention, the peptide toxin employed preferably has a cell destructive effect.

The substance having an antagonistic effect and/or the penetrant preferably is a phospholipase or a hyaluronidase or a combination of both substances. Also other substances different from phospholipases or hyaluronidases which have an antagonistic effect on the peptide toxin and/or act as a penetrant are comprised according to the invention. It is further preferred that the substance having an antagonistic effect is a mixture of phospholipases and hyaluronidases present in the poison of spiders of the species mentioned in this invention. In another embodiment the substance having an antagonistic effect and/or the penetrant is a phospholipase and/or hyaluronidase derived from an organism which is different from spiders of the family of Sicariidae, e.g. from other spider families or snakes. Preferably contained are hyaluronidases from snake poisons, preferably from Cobra poisons, or phospholipases from *Actrataspis bibronii, Bitis arietans*, or *Vipera aspis zinnikeri*. The penetrant preferably is a phospholipase.

Preferably, the peptide toxin and the substance having an antagonistic effect thereon and/or the penetrant are obtained from the spider poison by a fractionation procedure, and it is further preferred that the pharmaceutical composition contains a peptide toxin and a substance having an antagonistic effect thereon and/or a penetrant which are derived from different fractions. By this the efficacy of the pharmaceutical composition may be adjusted advantageously with respect to the tumor type and/or size to be treated.

The peptide toxin and the substance having an antagonistic effect thereon and/or the penetrant may be obtained from the raw spider poison mixture (spider poison cocktail) by fractionation procedures known per se for the separation of proteins. It is preferred to obtain the peptide toxin and the substance having an antagonistic effect thereon by gel chromatography, HPLC, affinity chromatography and/or ion exchange chromatography. The substance having an antagonistic effect and the penetrant may be obtained in the same manner also from other organisms.

It is additionally preferred that the peptide toxin and the substance having an antagonistic effect thereon and/or the penetrant are present in the pharmaceutical composition in an amount sufficient to provide a destructive effect of the peptide toxin and the substance having an antagonistic effect thereon and/or the penetrant with respect to tumor cells. The ratios and the amounts, respectively, of the peptide toxin and the substance having an antagonistic effect thereon is preferably chosen to ensure a controlled distribution in the tissue to be treated with respect to the temporal and/or spatial distribution. Furthermore, the amount chosen is such that the peptide toxin does exhibit no or only a slight toxic side effect in the patient to be treated. It has to be understood, however, that the amounts must be adjusted with respect to the tumor and the patient to be treated. The suitable amount of the individual substances and their proportions with respect to each other may be established by the skilled artisan in the frame of animal experiments and/or ethically reasonable studies with patients. Preferably, the amount of the penetrant is chosen to ensure that the penetrant principally recognizes all malignant cells and in combination with the peptide toxin selectively destroys the tumor cells while normal cells largely remain unaffected.

Further preferred is a pharmaceutical composition in which the amount of the peptide toxin and of the substance having an antagonistic effect thereon and/or the penetrant is selected to ensure a spatially and temporally controlled distribution.

Preferably, the pharmaceutical composition contains an amount of peptide toxin and substance having an antagonistic effect and/or penetrant which has been chosen in accordance with the tumor to be treated.

It is further preferred that the pharmaceutical composition contains conventional carriers and excipients. It is preferred that the pharmaceutical composition contains further active ingredients such as antibiotics, antimycotics, anti-tuberculosis agents, anti-parasite agents, cytostatics, amino acids, enzymes promoting wound-healing and/or mitosis inhibitors. In this respect penicillin/streptomycin, polymyxin/gentamycin, glutamine (5%), mitopodocide, Vinca rosea alkaloids, bromelaina, or bromelains are preferred.

The peptide toxin from the poison of spiders of the family of Sicariidae and the substance having an antagonistic effect thereon and/or the penetrant contained in the pharmaceutical preparation according to the present invention may be obtained by isolation procedures known per se. A preferred example for these is a fractionation method. The substances isolated in this way and obtained in a pure form by means of purification procedures may then be employed in a medical-therapeutical application. A preferred method will be detailed below.

It is also possible, however, to prepare the peptide toxin from the poison of spiders of the family of Sicariidae and the substance having an antagonistic effect thereon and/or the penetrant by chemical synthesis or by procedures of genetic engineering in a recombinant form. Typical for chemical substances, the present invention also comprises derivatives and salts of the substances provided according to the present invention. For example, the peptide toxin may comprise one or more amino acid additions, substitutions and/or deletions while, however, it must be ensured that the medical activity according to the present invention is preserved.

The preparation of the peptide toxin and of the substance having an antagonistic effect thereon and/or the penetrant is carried out by means of procedures conventional in chemical methodology. These include mainly fractionation techniques; however, also other methods may be used such as immunological procedures to "fish" the desired substances from the whole poison cocktail.

A preferred method for the preparation of a pharmaceutical composition according to the present invention which contains in a pharmaceutically effective amount at least a peptide toxin as well as at least a substance having an antagonistic effect thereon and/or at least a penetrant wherein the peptide toxin is derived from the poison of spiders of the family of Sicariidae and optionally the substance having an antagonistic effect thereon and/or the penetrant is derived from the poison of spiders of the family of Sicariidae, comprises the following steps:

preparing a raw spider poison mixture by procedures known per se and fractionating the mixture to obtain the peptide toxin and optionally the substance having an antagonistic effect thereon and/or the penetrant and optionally other substances in fractions which are separated from each other if possible;

combining different fractions of the peptide toxin with fractions containing substances having an antagonistic effect thereon and/or penetrants, or with substances having an antagonistic effect and/or penetrants derived from other organisms to obtain a pharmaceutically effective composition.

The spider poison contains various peptide toxins and various substances having an antagonistic effect thereon and/or penetrants, and optionally other active ingredients which are also relevant in a medical-therapeutical sense. All these substances may be used therapeutically in a pharmaceutical preparation in a specific ratio to be determined by the skilled artisan. While the experiments shown in the Examples are particularly directed to fractions 1 to 12, also the subsequent fractions of the fractionation method specifically described herein contain therapeutically effective substances. It has to be noted that the fractionation procedure merely shows a possibility of how the peptide toxins and the substances having an antagonistic effect thereon may be obtained in an exemplary manner. Also other embodiments are possible.

In this respect, it is preferred that the raw spider poison mixture is prepared from female spiders of the family of Sicariidae. This is advantageous because female spiders of the family of Sicariidae produce a higher amount of poison than male species.

It is further preferred that the raw spider poison mixture is obtained by manual milking. This is advantageous because the raw spider toxin mixture is obtained in a particularly careful manner.

Moreover, it is preferred in the method of the present invention to homogenize the raw spider poison mixture prior to fractionation, and it is further preferred to deep-freeze and further preferred to lyophilize the fractions prior to further processing.

The pharmaceutical compositions of the present invention are suitable for the use in medicine.

According to the present invention, the pharmaceutical compositions may be preferably used in the treatment of tumor diseases wherein a supportive treatment in the case of tumor operations is further preferred.

Specification

At present, about 35,000 species of Araneae exist worldwide. With the exception of approximately 300 species, all of these are actively poisonous animals using their poison for prey catching. Since spiders have only a very small mouth opening, they developed enzymes and poisons to digest their prey outside of the body so that the spiders aspirate the liquefied food. By their poisons, about 50 spider species may also be dangerous to humans. Despite of this, the poisons mainly of these species have been investigated only roughly or not at all. The main components of spider poisons are:

digestive enzymes
biogenic amines
organic acids
peptides
peptide toxins.

Among the peptide toxins, the following groups of toxins may be found:

heart toxins
nerve toxins
blood toxins
cell toxins
tissue-destructive poisons.

Initially, the whole poison cocktail of all actively poisonous animals usually achieves a pre-digestion and thereby a specific alteration of the original animal cells by means of an interplay of different substances.

In all spider species used in the present invention in the poison cocktail contains substances which act in a cytotoxic, necrotic and apoptotic manner (digestive action of the poisons). Besides, these also include stopper substances which have an antagonistic effect on these substances having a lytic effect, and/or penetrants.

Since spiders must ingest food which is still useful (whole protein structures and intact amino acids) they have developed their highly effective poison cocktail in the course of their evolution which lasted for 350 millions of years. Within this poison cocktail, the spatial distribution of the peptide toxin is limited depending on the factors of time and concentration by specifically acting enzymes in a controlled manner by an interaction of peptide toxins and substances having an antagonistic effect thereon.

Now, it has been surprisingly found that components of the spider toxins of spiders of the family of Sicariidae may be used for the treatment of tumor diseases.

Because of its lethal effect even in very small doses due to synergisms and antagonisms of various substances contained in the mixture, the poison cocktail as a whole is not useful for pharmaceutical purposes. Secreted by the spiders as a defense poison, one who has been bitten will suffer from the following symptoms:

The bite itself is not recognized by more than 90 percent of the persons bitten. After about 90 minutes a severely suppurating local necrosis of about 3 cm in diameter which already macerates through the skin will appear around the site of the bite. After about 2 hours the bite wound will break open locally, and early systemic effects will be recognized such as circulatory shock and/or heart arrhytmias. After the elapse of further 2–3 hours the lytic substances start their action.

The person bitten will have a strong precipitant urination, the urine being already hemorrhagic. Because poison has an organ necrotic effect, pains will spread throughout the whole abdomen. The liver is unable to metabolize poison in the concentrations and combinations delivered by the spider. If the spider has injected a large amount of poison during biting, the body is unable to manage its degradation and the patient will die because of kidney failure as a result of acute blood poisoning.

However, surprisingly, combinations of peptide toxins and enzymes with opposite action (which have an antagonistic effect on the peptide toxins) and/or penetrants contained in the spider poison wherein at least the peptide toxin and optionally the substance having an antagonistic effect thereon and/or the penetrant is derived from the poison of spiders of the family of Sicariidae may be used in appropriate concentrations and proportions in the treatment of tumor diseases as well as in parallel or in a supportive manner, respectively, in tumor operations, and (residual) tumor tissue may be destroyed. According to the invention, the destruction of tumor tissue which was not resected during operation as well as prevention of the formation of local tumor metastases in the organism may be for example achieved.

Mode of action of the substances used in combination with the peptide toxin:

Antagonistic effect: According to the present invention, tissue may be destroyed without complications in vitro in desired, locally restricted areas, particularly tumor cell predestinated areas. The mechanism of action in this case is based on the native, mutually interacting modes of action of the peptide toxins and of the substances having an antagonistic effect thereon present in the poison cocktail. According to the invention, substances having an antagonistic effect are meant to be substances which are able to digest or to decompose, respectively, the peptide toxin combined therewith. Experiments carried out with human cells revealed the following: a portion of the peptide toxins having a cell destructive effect is distributed in the cell culture faster than the enzymes which digest this toxin and therefore have an antagonistic effect thereon. Based on these findings, a quantitative composition of a combination of peptide toxin and substance having an antagonistic effect may be established depending on the nature and quantity of the tissue area to be lysed in order to achieve a controlled spatial and temporal destruction. By using simple determination of the molecular weight by means of electrophoresis, after contacting in solution the originally employed peptide toxins may no longer be detected in a pre/post contacting comparison (the respective band is missing). In the present invention, the substances having an antagonistic effect are meant to be for example phospholipases and hyaluronidases from spiders of the family of Sicariidae wherein it cannot be ruled out that further substances having an antagonistic effect are present in the spider toxin which may also be used according to the present invention.

Penetration (synergistic effect): The surface protein structure of genetically defective body cells or tumor cells, respectively, is altered (Lottspeich F., Zorbas H. (1998): Bioanalytik. Spektrum Akademischer Verlag Heidelberg Berlin). The phospholipases and/or hyaluronidases employed according to the present invention and optionally additional substances are able to recognize, selectively bind to, and lyse these tumor cells altered in their surface structure. According to the invention this particularly applies to phospholipases. Since the immunogenic state of the phospholipases of animal origin employed alone often is very low as is that of human phospholipases of cancer patients, phospholipases of other organisms, e.g. of spiders or snakes, may be used according to the present invention for the therapy approach for the treatment of tumor diseases. In has been shown by experiments that also non-self phospholipases derived from spider or snake toxins, respectively, not only recognize genetically defective human body cells but also are useful for the infiltration of peptides with necrotic or cytotoxic activities, respectively, to which they are coupled. These peptides, in the present case peptide toxins derived from the poisons of the family of Sicariide, if introduced into the cell, have a cell destructive effect. This effect presumably is an apoptosis because an important marker of apoptosis, caspase-3, may be measured in the medium (supernatant) after cell destruction.

According to the invention, penetrants are meant to be such substances which in combination with the peptide toxin selectively destroy the tumor cells and largely preserve the normal cells. Thus, according to the present invention, this also includes the ability of phospholipases, hyaluronidases and other substances contained in the poison to recognize malignant cells due to their altered surface structure and to dock to these cells and thereby loosen the cell wall, for example for the purpose of actively infiltrating substances which are coupled thereto (preferably peptide toxins having a cell destructive effect) into the malignant cell. In this respect, the penetrants used according to the present invention, particularly phospholipases, act as messengers and adjuvants (synergistic effect). According to the invention, penetration therefore does not refer to a permeability-enhancing effect which in the literature mostly is directed to an enhanced tendency for distribution within tissues.

The peptide toxins having a molecular weight of about 100 kDa have a tissue destructive effect. Because of their high molecular weight and their spatial structure they have a tendency of distribution within tissues of only about 100 cell layers per picogram of substance.

Optionally other substances contained in the raw spider poison mixture may contribute to the effects mentioned.

To avoid undesired cell destruction, an adjustment with respect to the absolute and relative amounts of the components of the peptide toxin/enzyme mixture depending on the type and size of the tumor to be treated may be made according to the present invention in vitro using living human cells (normal and malignant) of the tissue type to be treated. In this respect it is most important to determine the distribution tendency. This may be established in preliminary experiments by comparing the strength of the tumor tissues with that of the tissue surrounding the tumor (see also Example 2).

The mechanism of action of whole animal poison cocktails or of individual substances which have been separated therefrom by column chromatography and characterized via their molecular weight may be performed by testing these in appropriate normal and malignant human cell lines.

According to the present invention, at least the peptide toxin and optionally the substance having an antagonistic effect and/or the penetrant is derived from the poison of spiders of the family of Sicariidae. Preferred are the genera *Sicarius, Loxosceles, Scytodes* and/or *Drymusa*. Within the genus *Sicarius* use of the *Sicarius* spider species *Sicarius oweni, Sicarius testaceus, Sicarius hahni*, and *Sicarius albospinosus* is particularly preferred. Among the spiders of the genus *Loxosceles* the species *Loxosceles rufescens, Loxosceles reclusa*, and/or *Loxosceles laeta* may be used according to the present invention. Among the spiders of the genus *Scytodes* the species *Scytodes thoracica, Scytodes rufa*, and/or *Scytodes longipes* may be used according to the present invention.

According to the present invention, the peptide toxins are preferably derived from the same organism as the substances having an antagonistic effect thereon and/or the penetrants and other active substances which may be optionally contained. In this manner the effective interplay of these substances which has evolved in nature may be utilized.

In another preferred embodiment the substance having an antagonistic effect and/or the penetrant are derived from organisms which are different from spiders of the family of Sicariidae, for example from other spider families, snakes, scorpions etc. In these cases often larger amounts of the substances mentioned may be obtained. Example of such other organisms are cobras, *Actrataspis bibronii, Bitis arietans*, or *Vipera aspis zinnikeri*.

The pharmaceutical compositions according to the present invention may be prepared by first preparing a raw spider poison mixture from the spiders using methods known per se and performing a fractionation of the raw spider poison mixture by means of fractionation procedures also known per se for the separation of proteins to obtain the peptide toxins and the substances having an antagonistic effect thereon and/or the penetrants in a form separated from each other as much as possible or in separate fractions, respectively. Subsequently, to prepare a pharmaceutical composition different fractions of the peptide toxin may be combined with fractions containing substances having an antagonistic effect thereon and/or penetrants, or individual fractions of the peptide toxin may be combined with substances having an antagonistic effect and/or penetrants derived from different organisms. Preferably, also snake poisons such as the pit viper snake poison captopril may be contained as the peptide toxins.

Preferably, as the substances having an antagonistic effect also hyaluronidases from snake poisons, for example from cobra poisons, and/or as the penetrants phospholipases from *Actrataspis bibronii, Bitis arietans* or *Vipera aspis zinnikeri*, each in combination with one or more fractions of the Sicarius peptide toxin may be used.

For the preparation of pharmaceutical compositions it is also possible according to the invention to combine the fractions additionally with further useful active agents and/or with pharmaceutically conventional carriers and excipients.

For the preparation of the pharmaceutical compositions of the present invention, from the poison cocktail which may be obtained by manual milking of the spider species mentioned above there may be selected, for example via column chromatographic purification, specific poison components (peptide toxins with necrotic and cytotoxic action) as well as natural substances having an antagonistic effect thereon (stopper substances) and/or penetrants of the phospholipase and hyaluronidase type.

The analytics in order to differentiate between the components contained in the fractions may be performed via HPLC-MS-MS (e.g. using an apparatus of Perkin-Elmer company). It has been demonstrated by means of this analysis that based on their backbone structure analyzed by MS-MS the high molecular weight substances are enzymes of the phospholipase and hyaluronidase type. In addition to these enzymes there have also been found polypeptides which must be classified as peptide toxins due to their origin, mode of action and their NX, NHX, NOX, and SX type toxic groups revealed by MS-MS analysis.

The substances used for the pharmaceutical composition according to the present invention may be poisons naturally produced by Araneae of the genus *Sicarius* which originally have evolved for preying and pre-digestion of animal protein. This natural mode of action may be preserved by a function-preserving, careful preparation of the basic poison substance (e.g. by manual milking).

In contrast to conventional arthropod milking methods by means of an electrical procedure (Weickmann D. (1991): Haltung und Giftigkeit von Sicariidae. Arachnologischer Anzeiger 16:12–13; Weickmann D, Burda R. (1994): Electrophoresis of scorpion venoms. Electrophoresis Forum 1994, Abstracts, Technische Universität München, Oct. 24–26) in which the poison is removed from the animals by an electrical pulse inducing a contraction of the poison glands on the animals (for this purpose, the animals are preferably hypothermic), the poison cocktail is obtained according to the present invention via a manual procedure in which the animals are stimulated to deliver their poison by utilizing a natural defense behavior.

According to an embodiment of the present invention a manual milking method of the spiders is considered. This leads to the preparation of true and pure native poisons in contrast to for example the electrical milking method which due to the electron flow results in restructured substances and molecules, respectively, which may be altered in their action, and wherein substances may be contained in the poisons which the animal normally would not secrete. These substances may, but may not necessarily have a negative effect on the efficiency of the compounds contained in the poison cocktail having a medical effect. An standard analysis and/or quality control of the raw poison mixture may be performed via electrophoretic procedures.

The following Examples illustrate advantageous embodiments of the present invention, however, they should not be construed as limiting the scope of the present invention.

In the Examples and the Specification, reference is made to the following Figures:

FIG. 1 shows an SDS-PAGE electrophoresis (5 cm collecting gel, 15 cm separation gel, molecular weight range of 10 to 200 kDa) of whole poison cocktails from *Sicarius testaceus* and *Sicarius sp. Argentina*. Lanes 1 to 3 are molecular weight standards, lanes 4 and 5 are whole poison cocktails from *Sicarius testaceus*, and lane 6 is a whole poison cocktail from *Sicarius sp. Argentina*.

Figure 5:
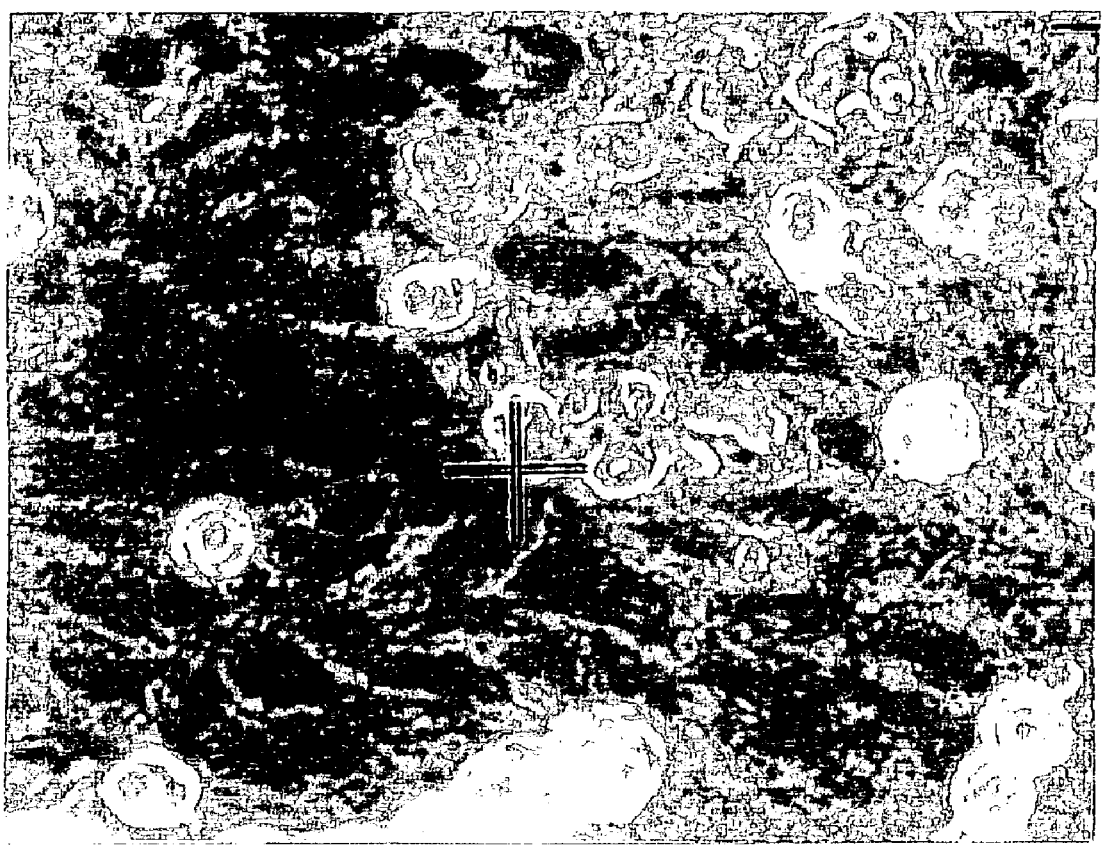

FIG. 5 demonstrates the selective action of a composition according to the present invention (Sic.Tox.2+Sic.Enz.4) on melanoma cells present in a skin cell culture.

Figure 6:
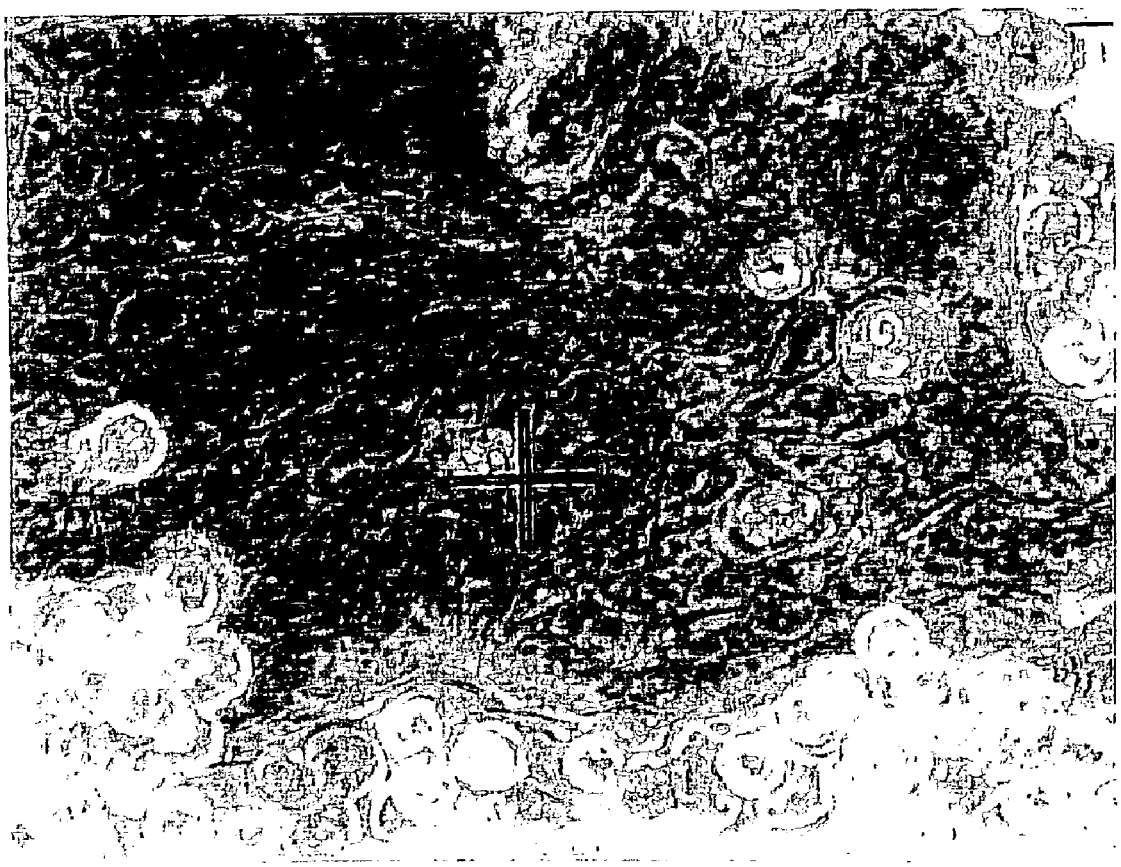

FIG. 6 shows the same area as in FIG. 5 but 3 hours after injection.

EXAMPLES

Example 1

Preparation of Pharmaceutical Compositions According to the Present Invention

For manual milking, subadult and adult females, respectively, of the *Sicarius* spider species *Sicarius oweni, Sicarius testaceus, Sicarius hahni*, or *Sicarius albospinosus* were fixed on their backs by the fingers of one hand while they were stimulated with the other hand using a sterile syringe (2 ml Brauninject of B. Braun company) and an adapted sterile needle (20 or 21 by Becton Dickinson) to secrete the poison at the chelicera by touching with the flat end of the needle at any time of the day at a room temperature of 21 to 27 degrees Centigrade and a humidity of 50 to 70% they.

In this respect, it was preferred that the stimulation period did not exceed 90 seconds since otherwise the animal would be subjected to unnecessary stress. After the poison drop appeared at the poison claws it was pulled into the syringe via the needle. A new syringe with new cannula was used for each animal. Afterwards the needle was closed again with its protective needle cap. Immediately afterwards, the closed syringe with the pulled up poison was placed in an exsiccator. This was stored for at least 12 hours in a deep-freeze cooled at at least minus 14 degrees Centigrade.

From the syringe with the frozen whole toxin, the protective needle cap was removed after it had been taken from the deep-freeze. The cannula was immersed in solvent such as protein solvent from Carl Roth GmbH & Co. KG (solvent for protein column chromatography: 0,25 M Tris/HCl, pH 6.5 to 7.3, 1.92 M glycine in destilled, deionized water/to prevent denaturation no SDS is used in the buffer) and 1 ml is pulled up. Thereby, poison is obtained in solution. Subsequently, the needle was removed. The individual poison solutions prepared in this way in syringes (5) were collected at room temperature by squirting out (syringing) into a sterile clean teflon vial. The sealed teflon vial was then shaken on a vortex mixer for 30 seconds without generation of foam whereby a homogenous solution was obtained.

After mixing, the entire solution was introduced via a Perspex funnel (to avoid contamination) into a fixed transparent Perspex column having an inner diameter of 1.5 cm, a wall thickness of 2 mm and a height of 50 cm tapering at the bottom to 1.5 mm, was open and filled with 20 ml gel (Sigma/Supelco company, AcA 34; matrix: 3% acrylamide/ 4% agarose; fractionation range (MW): proteins: 20 to 350 Da; cut off limit: 750 kDa; bead diameter: 60–140 micrometers). The poison solution introduced in this manner passed the gel and replaced the buffer present in the gel.

After the poison solution had completely soaked into the gel further 165 ml of solvent (0,25 M Tris/HCl, pH 6.5 to 7.3, 1.92 M glycine) were loaded onto the column. While passing through the gel this additional solvent replaces the poison solution contained therein. The first 15 ml which eluted at the bottom of the column were residual buffer and were discarded. Following this 15 ml, 40 fractions of 4 ml each were collected. The separation into 4 ml fractions each was due to the physical and chemical properties of the individual fractions as determined by electrophoresis, preferably SDS-PAGE. The loading buffers used for the protection of peptide bonds and proteins were Roti Load 1+2 (Carl Roth GmbH & Co. KG, Karlsruhe; SDS, glycerol, bromophenol blue, phosphate buffer, Roti Load 1 with mercaptoethanol, Roti Load 2 without mercaptoethanol). The individual fractions were collected separately in sterile clean 5 ml teflon vials with screw caps. Quality control of the individual fractions was carried out by electrophoresis.

For the pharmaceutical compositions of the present invention, different combinations of the fractions 1 to 12 were employed. These fractions contained spider poison protein components in a molecular weight range of about 75 to 175 kDa.

Figure 1:
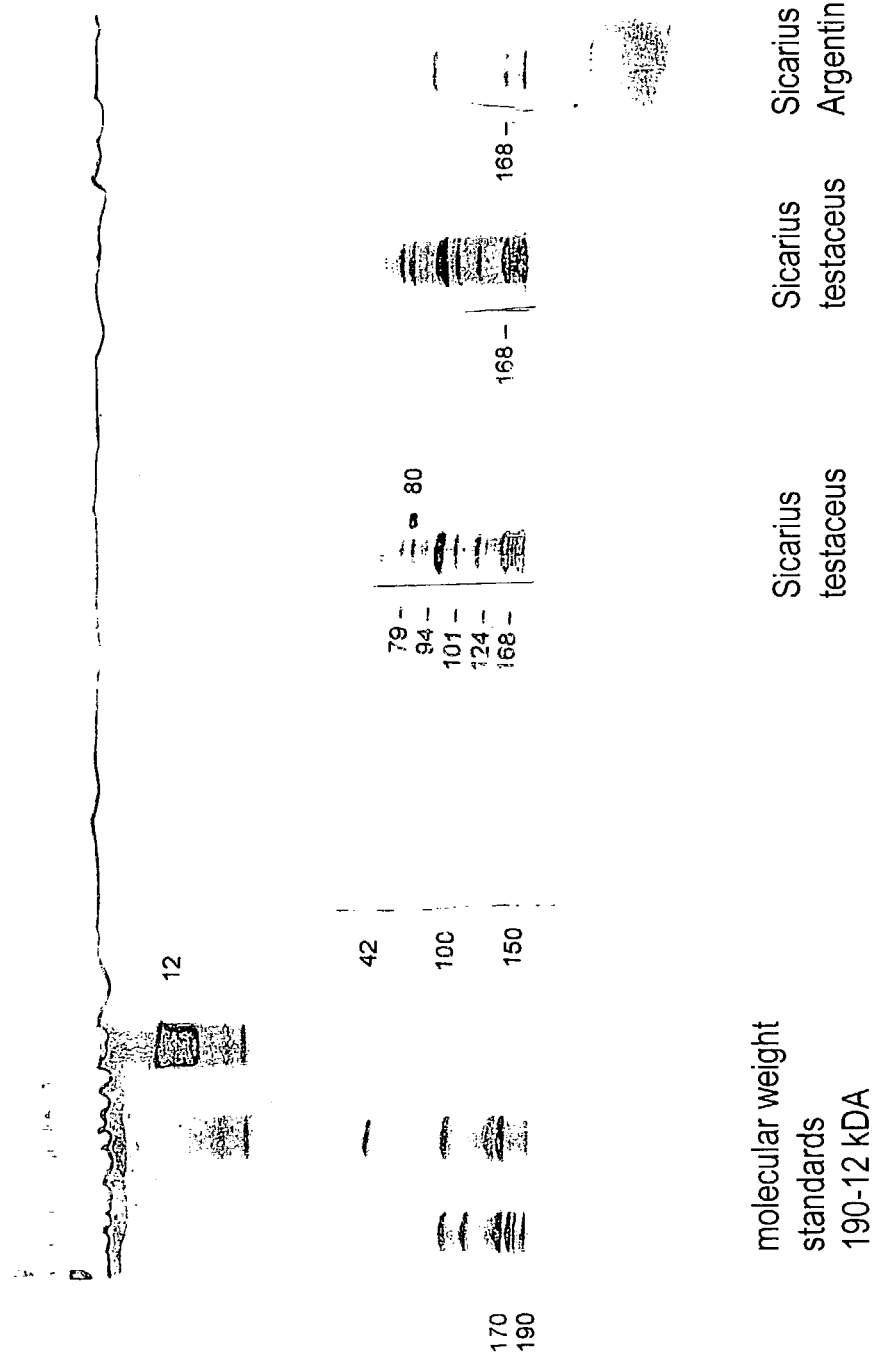
Figure 2:
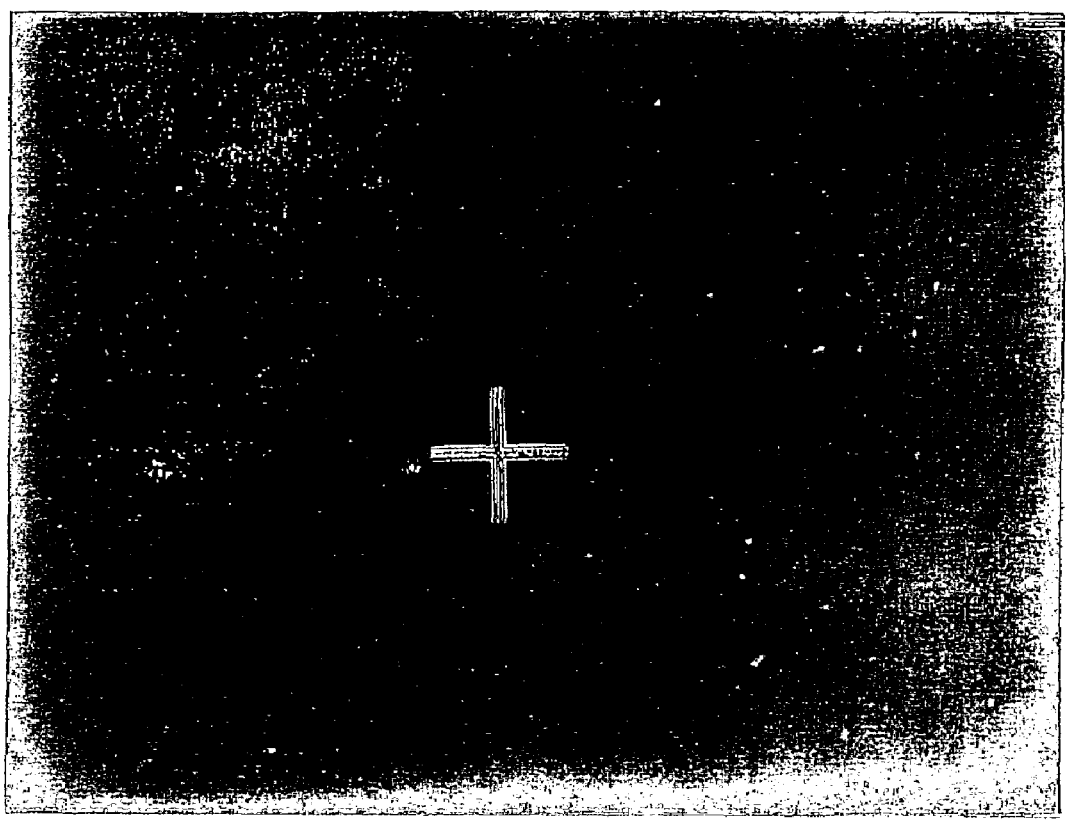
FIG. 2 shows the effect of a *Sicarius* whole poison cocktail on a mixed culture of normal skin cells with melanoma cells.
Figure 3:
FIG. 3 shows a light micrograph illustrating the effect of a composition according to the present invention (Sic.Tox.3+Sic.Enz.1) on mamma carcinoma cells present in a breast tissue culture 48 hours following injection.
Figure 4:
FIG. 4 shows the same area as in FIG. 3 but 72 hours after injection of the substance combination (Sic.Tox.3+Sic.Enz.1).

An SDS-PAGE electrophoresis of the whole poison cocktail of *Sicarius testaceus* is shown in FIG. 1.

To clarify the structure of the substances, the individual fractions were investigated by HPLC-MS-MS as well as by DAD-UV spectrometry (DAD or DADI, respectively: Direct Analysis of Daughter Ions). Known substances could not be detected in a higher molecular weight range (above 10,000 Da). However, the determinations of the backbone structure indicate that the substances belong to the type of polypeptide with toxic components (=polypeptide toxins) and on the other hand to the phospholipase and hyaluronidase type.

Fractions with similar composition may be collected together. For further processing and storage, the individual fractions were lyophilized, using for example the following parameters:

The fraction to be lyophilized was cooled to minus 22 degrees Centigrade in an open teflon vial covered with perforated aluminium foil. To ensure that the sample is frozen a cooling period of 11 hours was kept. Then, a vacuum of 0.200 mbar was established. After the vacuum was reached the fraction was warmed up to 4 degrees Centigrade and kept at this temperature for at least 24 hours while the vacuum was maintained. After the lyophilization procedure, the teflon vial containing the lyophilized fraction was screwed up airtight. The storage stability at room temperature is about 3 month, about 1 year at plus 7 degrees Centigrade, and about 5 years at minus 14 degrees Centigrade.

Substance content, effect and molecular weight of the fractions are shown in the following Table.

TABLE 1

| Fraction No. | mL from to | Substance description | Substance effect Cell toxin[1] | Substance effect Enzyme[1] | Molecular Weight kDa[2] |
|---|---|---|---|---|---|
| 1 | 1–4 | Sic. Tox. 1 | X | | approx. 72 |
| 2 | 5–8 | Sic. Tox. 2 | X | | approx. 79–80 |
| 3 | 9–12 | Sic. Enz. 1 | | X | |
| 4 | 13–16 | Sic. Tox. 3 | X | | approx. 94 |
| 5 | 17–20 | Sic. Enz. 2 | | X | |
| 6 | 21–24 | Sic. Enz. 3 | | X | |
| 7 | 25–28 | Sic. Tox. 4 | X | | approx. 101 |
| 8 | 29–32 | Sic. Enz. 4 | | X | |
| 9 | 33–36 | Sic. Tox. 5 | X | | approx. 124 |
| 10 | 37–40 | Sic. Tox. 6 | X | | approx. 168 |
| 11 | 41–44 | Sic. Enz. 5 | | X | |
| 12 | 45–48 | Sic. Enz. 6 | | X | |

[1] substance effect determined via GC-MS-MS or by in vitro experiments using different cell lines (see Example 2)
[2] Molecular weight determined via HPLC-MS Using the purification parameters cited in this Example this elution profile and the compositions of the fractions were mostly reproducible.

Fractions 13–40 have a molecular weight of up to about 350 kDa. The higher the molecular weight of these poison components, the more difficult is it to solubilize them for further investigations. Preliminary experiments, however, have shown that the total residual fraction (13–40) is for example able to lyse human periosteum cells. Furthermore the degradation of collagens can be observed in tests of the residual poison cocktail on various human cell lines. Moreover, it could be demonstrated via their effect that they contain insectotoxins. The soluble portion of these fractions is destructive for drosophila, schistocera and locusta cell lines. While as a result of these preliminary experiments at present it may not be expected that one or ore of the fractions 13 to 40 contain substances which may be used for the pharmaceutical compositions according to the present invention, however, this cannot be ruled out according to the present invention.

Example 2

Tumor Cell Destructive Activity of the Pharmaceutical Compositions According to the Present Invention Due to the numerous types of pathogeneses of tumor diseases it is currently impossible to provide a comprehensive preventive therapy. Thus, in the case of locally diagnosed tumors (primary or subsequent) operative resection is the first measure. A problem encountered in this respect is metastasis if incompletely removed tumor tissue is contacted with air upon resection. This problem may be overcome by applying pharmaceutical compositions according to the invention onto the cut surfaces during an operative tumor resection.

For the experimental series described below, the following tumor cell lines were used:

Mamma ca mixed cell culture: this cell type was cultured starting with of a tumor cell mixture derived from 11 female patients and studied since 1989 in long-term cultures and subcultures.

Lung ca: 2 cell lines (1 male and 1 female patient) identified by the laboratory of Weißenburg hospital and also studied in long-term culture and subculture since 1987.

Malig. melanoma: cells truly identified as such obtained from the patient by arrangement, also studied in long-term culture and subculture since 1995.

Prostate adenoma: Mixed cell culture of 3 patients, studied in long-term culture and subculture since 1988. Up to now, no therapeutical success in vitro.

Uterine ca: mixed cell culture of 5 patients cultured since August 2000.

Ovary ca: mixed cell culture of 3 patients cultured since August 2000.

Adeno ca: mixed cell culture of 3 patients cultured since August 2000.

Liver metastases: mixed cell culture of 2 patients starting from small cell bronchial carcinoma; cultured since September 2000.

Lung metastases: mixed cell culture of 2 patients starting from mamma ca as the primary tumor; cultured since August 2000.

a) Effect of the Whole Poison Cocktail

At the beginning of the experimental series, the milked fresh or solubilized whole poison cocktail and its activity depending on the concentration was tested on different cell lines. In these tests, no satisfactory results could be achieved because the poison in all cases killed the whole cell cultures while the time necessary for killing decreased with increasing concentration of the poison employed.

The effect of the whole poison cocktail from *Sicarius* on a mixed culture of normal skin cells with melanoma cells has been depicted exemplarily in FIG. 2. The culture medium was DMEM/Ham's F-12. Only occasional light and dark patches are observed which represent cell residues. These are the only remainders found at the bottom of the culture flask about 11 hours following injection of the whole poison cocktail.

b) Effect of Different Individual Fractions of the *Sicarius* Spider Poison Cocktail Experimental Procedure:

To detect the cell-destructive substance or substances, respectively, the whole poison cocktail was fractionated by column chromatography as described in Example 1 and a molecular weight determination of the individual components was performed by electrophoresis. The individual fractions (40 on average) were comparatively tested on related cell culture lines, i.e. on normal cell lines in comparison to the corresponding tumorous/malignant cells under the same conditions. For this purpose, in each case tumor cells were introduced in certain areas into cultures of normal cells. Subsequently, the fractions dissolved in isotonic saline were applied to (injected into) the areas with tumor cells and, for comparison also applied to (injected into) areas with normal cells, and the effect on the cells treated was observed in a light microscope.

Thereby, it was observed that about 40% of the substances tested present in the individual fractions have a tissue destructive activity. Moreover, these substances are able to lyse particular areas covered with tumor cells in vitro in a concentration-dependent manner. After the poisons had been washed out by the usual medium change these areas were again overgrown. Only in 1 of 8 cultures (12.5%) malignancy of the cells was again observed.

c) Effect of Combinations of Different Fractions of the *Sicarius* Spider Poison Cocktail As described above, the substances having an antagonistic effect have been found to be substantially enzymes of the hyaluronidase and phospholipase type.

Since these types of enzymes have also been referred to as penetration enzymes and since particularly the phospholipases are present in the organism as immunological auxiliary agents against genetically defective cells, experiments using substance combinations of the enzymes and peptide toxins were then conducted. For this purpose, the experiments were first conducted with fractions 1–12 because of their better handling. The experiments were performed as described in Example 2b), however, combinations of fractions were used instead of individual fractions. The solvent was again isotonic saline.

Pharmaceutical Composition Containing Substance Combination 1:

Substance combination 1 contained 10% by wt. of Sic.Enz.2, 15% by wt. of Sic.Tox.5, and 75% by wt. of an isotonic saline.

The activity of substance combination 1 (see also Table 4, EXP.5) on mamma ca cells co-cultured with breast tissue cells was such that following injection of the substance combination into the area of mamma ca cells all breast cancer cells were destroyed while the normal breast tissue cells were spared. Moreover, it was observed that the area lysed by substance combination 1 was again overgrown.

Due to the molecular structure and physical properties of substance combination 1 the cancer cell is traced down and recognized by the enzymes because of their natural properties. It may be assumed that the peptide toxins destroy cancer cell communication (destruction of transmitters) upon invading the cancer cell. Due to their molecular structure most of the peptide toxins present in *Sicarius* toxin attack proteins and proteinaceous compounds, respectively. Cancer cells have developed an intriguing defense mechanism against the body's own immune system of their host/carrier wherein mediators such as interferons, tumor necrosis factor and cytokines play an essential role. Since these mediators are present in the liquid medium they present optimal targets of an attack by the peptide toxins also employed in the liquid medium. Because there is evidence that the cancer cells severely affected by the peptide toxins of the present invention are no longer proliferation competent and adjacent cancer cells are unable to develop protective mechanisms against the peptide toxins there must be assumed that the mutual communication between the cancer cells has been destroyed.

In pharmaceutical compositions which contain substance combination 1 the enzymes are strongly enriched relative to the total composition.

Pharmaceutical Composition Containing Substance Combination 2:

Substance combination 2 contained 5% by wt. of Sic.Enz.1, 5% by wt. of Sic.Tox.3, and 90% by wt. of isotonic NaCl solution.

Using substance combination 2 a general cell destruction may be achieved which may be spatially limited in an optimal manner. The peptide toxins selected are able to destroy the tissue treated. Admixture of the natural peptide-degrading enzymes controls the spatial and temporal cell-destructive action of the peptide toxins.

The effect of substance combination 2 on mamma carcinoma cells present in a breast tissue cell culture is shown in FIGS. 3 and 4. The micrograph shown in FIG. 3 shows normal breast tissue cells cultured in DMEM/Ham's F-12 medium. The left half of the micrograph originally showed growing mamma carcinoma which were destroyed by the peptide/enzyme combination and purged by the second medium change after 48 hours. The normal cells were not affected and start to grow into the resulting space. FIG. 4 shows the same section as FIG. 3 but 72 hours after the injection. The area to the left which was empty previously starts to be overgrown by normal cells (next to the cross). First, it can be noticed that a loose cell assembly is developed which then is completed by true tissue.

These examples show that the use of combinations 1 or 2 may be selected depending on the type, size, and localization of the tumor to be removed. The substance combinations 1 and 2 may be applied to the cut surfaces during tumor resections. The use of combination 1 may be advantageous in operations where as little as possible adjacent normal tissue shall be destroyed. The use of substance combination 2 may be advantageous in operations in which not so much care has to be taken on the surrounding tissue.

The surgeon mixing the substances may refer with respect to their nature and quantity according to the type and localization of the tumor to the accompanying illustrative Tables 2 and 3 which contain an additional substance combination 3.

TABLE 2

| Tumor type | Substance mixture |
|---|---|
| Mamma ca | S 1 |
| Lung ca | S 2 |
| Melanoma, malig | S 3 |

S 1 = Sic.Enz.2 + Sic.Tox.5
S 2 = Sic.Enz.1 + Sic.Tox.3
S 3 = Sic.Enz.4 + Sic.Enz.5. + Sic.Tox.6

TABLE 3

Solution ratio in isotonic saline (M/V)

| mixture | Substance Tumor size in mm 0–1 | 2–3 | 4–5 | 6–10 | Substance % | Substance % | Substance % |
|---|---|---|---|---|---|---|---|
| S 1 | | | X | | 10 | 15 | — |
| S 2 | | X | | | 5 | 5 | — |
| S 3 | | | | X | 20 | 15 | 15 |

Experiments to Determine the Mode of Action of Other Substance Combinations

The efficacies of other substance combinations on mamma ca cells, lung ca cells, melanoma cells, uterine ca cells, ovarian ca cells, adeno ca cells, liver metastases derived from small cell bronchial carcinoma as the primary tumor, and lung metastases derived from mamma ca as the primary tumor are shown in the Tables 4 to 12 presented below. The experiments were performed as described above. The amounts of substances employed in these experiments were: 2 mg of peptide toxin and 2 mg of enzyme/100 ml 0.9% saline.

FIGS. 5 and 6 exemplarily show the effect of the substance combination (Sic.Tox.2+Sic.Enz.4) shown in Table 7 on melanoma cells. The micrograph shows an area of a skin cell culture grown in DMEM/Ham's/F12 into which melanoma cells derived from the same individual were injected at various sites 30 minutes after injection of the peptide toxin/enzyme combination. In the center of the micrograph irregular melanoma cells are still visible all of which are under lysis upon injection of the poison. Individual rounded normal skin cells were not attacked by the peptide toxin/enzyme mixture and therefore are still visible. FIG. 6 shows the same area as FIG. 5 but 3 hours after the injection. It is obvious that all tumor cells have been lysed. At the border between the tumor area and normal tissue only normal skin cells are visible, and in the former tumor area individual normal skin cells may be seen.

Furthermore, it has been found that in long-term cultures (thicker cell layer in vitro) also a destruction of tumor tissue in lower cell layers could be achieved if the enzymes were added in higher concentrations and these obviously made the tissue more permeable to the poisons and, because of their specificity, made the genetically defective cells susceptible to the poison.

The results of the impact of different substance combinations on different cell lines is summarized in Tables 4 to 7.

TABLE 4

Mamma Ca

| Experiment No. | Substance combination | Result |
|---|---|---|
| EXP. 1 | Sic.Tox.1 + Sic.Enz.2 | All breast cancer cells killed |
| EXP. 2 | Sic.Tox.2 + Sic.Enz.2 | All breast cancer cells killed |
| EXP. 3 | Sic.Tox.3 + Sic.Enz.2 | No effect on cells observed |
| EXP. 4 | Sic.Tox.4 + Sic.Enz.2 | No effect on cells observed |
| EXP. 5 | Sic.Tox.5 + Sic.Enz.2 | All breast cancer cells killed, destroyed lysed area is overgrown |
| EXP. 6 | Sic.Tox.6 + Sic.Enz.2 | No effect on cells observed |

TABLE 5

Mamma Ca

| Experiment No. | Substance combination | Result |
|---|---|---|
| EXP. 1 | Sic.Tox.1 + Sic.Enz.1 | All cells killed |
| EXP. 2 | Sic.Tox.2 + Sic.Enz.1 | No effect on cells observed |
| EXP. 3 | Sic.Tox.3 + Sic.Enz.1 | All breast cancer cells killed; no effect on breast cells observed |
| EXP. 4 | Sic.Tox.4 + Sic.Enz.1 | No effect on cells observed |
| EXP. 5 | Sic.Tox.5 + Sic.Enz.1 | No effect on cells observed |
| EXP. 6 | Sic.Tox.6 + Sic.Enz.1 | All cells killed |
| EXP. 7 | Sic.Tox.7 + Sic.Enz.1 | All cells detached and become black |

TABLE 6

Lung Ca

| Experiment No. | Substance combination | Result |
|---|---|---|
| EXP. 1 | Sic.Tox.1 + Sic.Enz.6 | All cells in the culture are killed |
| EXP. 2 | Sic.Tox.2 + Sic.Enz.6 | All lung cancer cells are killed. Destroyed lysed area is very well overgrown. |
| EXP. 3 | Sic.Tox.3 + Sic.Enz.6 | All lung cancer cells are killed. Destroyed lysed area is very well overgrown. |
| EXP. 4 | Sic.Tox.4 + Sic.Enz.6 | All lung cancer cells are killed. Destroyed lysed area is overgrown |
| EXP. 6 | Sic.Tox.6 + Sic.Enz.6 | No effect on cells observed |

TABLE 7

Melanoma cells

| Experiment No. | Substance combination | Result |
|---|---|---|
| EXP. 1 | Sic.Tox.1 + Sic.Enz.4 | No effect on cells observed |
| EXP. 2 | Sic.Tox.2 + Sic.Enz.4 | All melanoma cells are killed. The lysed area is overgrown by normal skin tissue |
| EXP. 3 | Sic.Tox.3 + Sic.Enz.4 | All melanoma cells are killed. The lysed area is not overgrown |
| EXP. 4 | Sic.Tox.4 + Sic.Enz.4 | All skin cells are killed |
| EXP. 5 | Sic.Tox.5 + Sic.Enz.4 | All skin cells are killed |
| EXP. 6 | Sic.Tox.6 + Sic.Enz.4 | No effect on cells observed |

TABLE 8

Uterine ca mixed cell culture of 5 patients

| Experiment No. | Substance combination | Result |
|---|---|---|
| EXP. 1 | Sic.Tox.1 + Sic.Enz.2 | All malignant uterine cells are killed. |
| EXP. 2 | Sic.Tox.2 + Sic.Enz.2 | No effect on cells observed |
| EXP. 3 | Sic.Tox.3 + Sic.Enz.2 | No effect on cells observed |
| EXP. 4 | Sic.Tox.4 + Sic.Enz.2 | No effect on cells observed |
| EXP. 5 | Sic.Tox.5 + Sic.Enz.2 | No effect on cells observed |
| EXP. 6 | Sic.Tox.6 + Sic.Enz.2 | No effect on cells observed |

TABLE 9

Ovarian ca mixed cell culture of 3 patients

| Experiment No. | Substance combination | Result |
|---|---|---|
| EXP. 1 | Sic.Tox.1 + Sic.Enz.2 | All ovarian ca cells are killed. |
| EXP. 2 | Sic.Tox.2 + Sic.Enz.2 | No effect on cells observed |
| EXP. 3 | Sic.Tox.3 + Sic.Enz.2 | No effect on cells observed |
| EXP. 4 | Sic.Tox.4 + Sic.Enz.2 | No effect on cells observed |
| EXP. 5 | Sic.Tox.5 + Sic.Enz.2 | No effect on cells observed |
| EXP. 6 | Sic.Tox.6 + Sic.Enz.2 | No effect on cells observed |

TABLE 10

Adeno ca mixed cell culture of 3 patients

| Experiment No. | Substance combination | Result |
|---|---|---|
| EXP. 1 | Sic.Tox.1 + Sic.Enz.6 | No effect on cells observed |
| EXP. 2 | Sic.Tox.2 + Sic.Enz.6 | No effect on cells observed |
| EXP. 3 | Sic.Tox.3 + Sic.Enz.6 | No effect on cells observed |
| EXP. 4 | Sic.Tox.4 + Sic.Enz.6 | All adeno ca cells were lysed. The destroyed lysed cell area is slowly overgrown with normal surrounding cells. |
| EXP. 5 | Sic.Tox.5 + Sic.Enz.6 | No effect on cells observed |
| EXP. 6 | Sic.Tox.6 + Sic.Enz.6 | No effect on cells observed |

TABLE 11

Liver metastases derived from a small cell bronchial carcinoma as the primary tumor. Mixed cell culture of 2 patients

| Experiment No. | Substance combination | Result |
|---|---|---|
| EXP. 1 | Sic.Tox.1 + Sic.Enz.1 + Sic.Enz.6 | No effect on cells can be observed |
| EXP. 2 | Sic.Tox.2 + Sic.Enz.1 + Sic.Enz.6 | All liver metastases cell clusters were lysed. These empty cell areas are again overgrown from the outside to the inside with normal surrounding tissue |
| EXP. 3 | Sic.Tox.3 + Sic.Enz.1 + Sic.Enz.6 | Result as in Exp. 2 with clearly improved regeneration of the normal tissue |
| EXP. 4 | Sic.Tox.4 + Sic.Enz.1 + Sic.Enz.6 | No effect on cells observed. |
| EXP. 5 | Sic.Tox.5 + Sic.Enz.1 + Sic.Enz.6 | No effect on cells observed. |
| EXP. 6 | Sic.Tox.6 + Sic.Enz.1 + Sic.Enz.6 | No effect on cells observed. |

TABLE 12

Lung metastases derived from a mamma carcinoma as the primary tumor. Mixed cell culture of 2 patients

| Experiment No. | Substance combination | Result |
|---|---|---|
| EXP. 1 | Sic.Tox.1 + Sic.Enz.1 + Sic.Enz.6 | No effect on cells can be observed |
| EXP. 2 | Sic.Tox.2 + Sic.Enz.1 + Sic.Enz.6 | The secondary tumor cell clusters initiated by the lung metastases were completely lysed. After a twofold medium change the empty cell areas are again overgrown with intact lung tissue cells. |
| EXP. 3 | Sic.Tox.3 + Sic.Enz.1 + Sic.Enz.6 | No effect on cells observed. |
| EXP. 4 | Sic.Tox.4 + Sic.Enz.1 + Sic.Enz.6 | No effect on cells observed. |
| EXP. 5 | Sic.Tox.5 + Sic.Enz.1 + Sic.Enz.6 | No effect on cells observed. |
| EXP. 6 | Sic.Tox.6 + Sic.Enz.1 + Sic.Enz.6 | No effect on cells observed. |

Example 3

Enzyme/Peptide Toxin Blocking Tests

Further experiments were conducted in order to test whether certain enzyme fractions neutralize particular peptide toxin fractions at given concentrations of peptide toxin and enzyme.

Experimental Procedure:

In the experiments summarized in the following Tables 13 and 14, breast tissue cells, mamma ca cells, skin cells, stem cells, liver cells, lung cells, and lung ca cells as well as a PHA-stimulated mixed cell culture from various skin cell lines were used.

The cells tested were added with 3 ml of a solution of 2 mg enzyme/100 ml medium (DMEM/Ham's F-12 with about 1.2% glutamine, 2.5% penicillin/streptomycin, and 10% fetal calf serum). After 12 hours, 3 ml of a peptide toxin solution (2 mg peptide toxin/100 ml 0.9% saline) were added. The effects on the cells contained in the cell culture flask were observed by light microscopy. If a neutralization/blockage of the peptide toxins occurred this was seen by the absence of a noticeable effect of the peptide toxin on the cells present in culture since it was neutralized immediately by the enzyme.

If this was not the case, a destruction/lysis of the cells occurred.

The results summarized in the following tables indicate that in the concentrations chosen and for the cell lines specified above particular enzymes always specifically neutralize the same peptide toxins. Thus, in these concentration ratios a use of these combinations in the above-mentioned cell lines seems to be advantageous since a broad spatial distribution of the peptide toxins may be avoided. However, the results may be different if the enzyme and peptide concentrations are altered and other cell lines are used.

Tables 13 and 14: Enzyme/Peptide Toxin Blocking Tests

TABLE 13

| Experiment No. | Substance combination | Result |
|---|---|---|
| EXP. 1 | Sic.Tox.1 + Sic.Enz.1 | Poison effect of Tox.3 is neutralized with Enz.1 |
| | Sic.Tox.2 + Sic.Enz.1 | |
| | Sic.Tox.3 + Sic.Enz.1 | |
| | Sic.Tox.4 + Sic.Enz.1 | |
| | Sic.Tox.5 + Sic.Enz.1 | |
| | Sic.Tox.6 + Sic.Enz.1 | |
| EXP. 2 | Sic.Tox.1 + Sic.Enz.2 | Poison effect of Tox.5 is neutralized with Enz.2 |
| | Sic.Tox.2 + Sic.Enz.2 | |
| | Sic.Tox.3 + Sic.Enz.2 | |
| | Sic.Tox.4 + Sic.Enz.2 | |
| | Sic.Tox.5 + Sic.Enz.2 | |
| | Sic.Tox.6 + Sic.Enz.2 | |
| EXP. 3 | Sic.Tox.1 + Sic.Enz.3 | Poison effect of Tox.1 and also of Tox.2 is neutralized with Enz.1 |
| | Sic.Tox.2 + Sic.Enz.3 | |
| | Sic.Tox.3 + Sic.Enz.3 | |
| | Sic.Tox.4 + Sic.Enz.3 | |
| | Sic.Tox.5 + Sic.Enz.3 | |
| | Sic.Tox.6 + Sic.Enz.3 | |

TABLE 14

| Experiment No. | Substance combination | Result |
|---|---|---|
| EXP. 4 | Sic.Tox.1 + Sic.Enz.4 | Poison effect of Tox.2 and also of Tox.3 is neutralized with Enz.4 |
| | Sic.Tox.2 + Sic.Enz.4 | |
| | Sic.Tox.3 + Sic.Enz.4 | |
| | Sic.Tox.4 + Sic.Enz.4 | |
| | Sic.Tox.5 + Sic.Enz.4 | |
| | Sic.Tox.6 + Sic.Enz.4 | |
| EXP. 5 | Sic.Tox.1 + Sic.Enz.5 | Poison effect of Tox.6 and also of Tox.1 and Tox.5 neutralized with Enz.5 |
| | Sic.Tox.2 + Sic.Enz.5 | |
| | Sic.Tox.3 + Sic.Enz.5 | |
| | Sic.Tox.4 + Sic.Enz.5 | |
| | Sic.Tox.5 + Sic.Enz.5 | |
| | Sic.Tox.6 + Sic.Enz.5 | |
| EXP. 6 | Sic.Tox.1 + Sic.Enz.6 | Poison effect of Tox.4 and also of Tox.2 and Tox.3 neutralized with Enz.6 |
| | Sic.Tox.2 + Sic.Enz.6 | |
| | Sic.Tox.3 + Sic.Enz.6 | |
| | Sic.Tox.4 + Sic.Enz.6 | |
| | Sic.Tox.5 + Sic.Enz.6 | |
| | Sic.Tox.6 + Sic.Enz.6 | |

Example 4

Combination with Snake Venom Phospholipases

Further experiments revealed that for individual *Sicarius* toxins also specific phospholipases from the whole poison cocktail of snakes could be used as antagonists.

It is known that enzymes of the hyaluronidase and phospholipase type (e.g. phospholipase A1, phospholipase D-B, phospholipase E) are also contained in the whole poison cocktail of snakes (Hankin E. H. (1899): The action of cobra poison on the blood (Path & Bact.). Originally in II. of Path. and Bact. 1897/Hankin E. H. (1900): The haemolytic action of snake toxins and toxic p. sera, 450. Med. Gazette/Dennys G. W. P. (1916): Experiments with snake venoms and some important notes. Med. Gazette/Ardeshire K. (1918): Bite from *Echis carinata*-recovery (corr.). Med. Gazette/Neuberg Rosenberg (1907): Lipolyse, Agglutination und Hämolyse. B. kl. W./Lamb and Hunler (1904–1907): Actions of venoms of different species of poisonous snakes and the nervous system. Lancet/Lindemann W. (1898): Über die Sekretionserscheinungen der Giftdrüse der Kreuzotter. Arch. f. mikr. Anat.) and own experiments (Burda R., Richter R., Schrottenloher E., Weickmann D. (2001): Visueller Schnellnachweis für Enzyme in Schlangengiften unter Zuhilfenahme eines Schwarzweißfilmes, in press).

Because snake venoms may be prepared in larger amounts and the percentage of the enzymes contained therein is higher, the antagonistic effect of individual enzyme fractions from snake venoms was tested on the *Sicarius* toxins. In these experiments the following results were obtained.

TABLE 15

Enzyme/peptide toxin blocking tests

| Experiment No. | Substance combination | Result |
|---|---|---|
| EXP. 1 | Sic.Tox.1 + AtractaspisEnz.1 | Poison effect of Sic.Tox.1 is neutralized with AtractaspisEnz.1 |
| | Sic.Tox.2 + AtractaspisEnz.1 | |
| | Sic.Tox.3 + AtractaspisEnz.1 | |
| | Sic.Tox.4 + AtractaspisEnz.1 | |
| | Sic.Tox.5 + AtractaspisEnz.1 | |
| | Sic.Tox.6 + AtractaspisEnz.1 | |

TABLE 15-continued Enzyme/peptide toxin blocking tests

| Experiment No. | Substance combination | Result |
|---|---|---|
| EXP. 2 | Sic.Tox.1 + Bit.Phos.A2<br>Sic.Tox.2 + Bit.Phos.A2<br>Sic.Tox.3 + Bit.Phos.A2<br>Sic.Tox.4 + Bit.Phos.A2<br>Sic.Tox.5 + Bit.Phos.A2<br>Sic.Tox.6 + Bit.Phos.A2 | Poison effect of Sic.Tox.3 neutralized with Bit.Phos.A2 |
| EXP. 3 | Sic.Tox.1 + Bit.Phos.D<br>Sic.Tox.2 + Bit.Phos.D<br>Sic.Tox.3 + Bit.Phos.D<br>Sic.Tox.4 + Bit.Phos.D<br>Sic.Tox.5 + Bit.Phos.D<br>Sic.Tox.6 + Bit.Phos.D | Poison effect of Sic.Tox.6 neutralized with Bit.Phos.D |
| EXP. 4 | Sic.Tox.1 + Vip.asp.Phos.A1<br>Sic.Tox.2 + Vip.asp.Phos.A1<br>Sic.Tox.3 + Vip.asp.Phos.A1<br>Sic.Tox.4 + Vip.asp.Phos.A1<br>Sic.Tox.5 + Vip.asp.Phos.A1<br>Sic.Tox.6 + Vip.asp.Phos.A1 | Poison effect of Sic.Tox.4 neutralized with Vip.asp.Phos.A1 |

Sic.Tox. in each case is as defined above.

AtractaspisEnz.1 denotes an A type phospholipase from the poison of *Atractaspis bibronii*.

Bit.Phos.A2 means the phospholipase A2 from the venoms of the dark colored South African populations of *Bitis arietans* (possible a different species, *Bitis lachensis* as proposed earlier)

Bit.Phos.D denotes the phospholipase D from the venoms of the dark colored South African populations of *Bitis arietans* (possible a different species, *Bitis lachensis* as proposed earlier)

Vip.asp.Phos.A1 means the phospholipase from the venoms of *Vipera aspis zinnikeri*

Example 5

Experiments with Fractions Derived from Other Sicariidae Spider Species

*Sicarius oweni*

In this case, a toxin of *Sicarius oweni* of 69 kDA having similar mamma ca-destructive properties as Sic.Tox.1 with about 72 kDA and Sic.Tox.5 with about 124 kDA of *Sicarius testaceus* was tested among others. As the phospholipase for combination there may be used the enzyme fraction of *Sicarius oweni* which elutes from the column after about 21–24 ml. The fractions are denoted as in the case of *Sicarius testaceus*.

TABLE 16

Mamma ca with fractions from the poison of *Sicarius oweni*

| Experiment No. | Substance combination | Result |
|---|---|---|
| EXP. 1 | Sic.Tox.1 + Sic.Enz.1 | No effect on the cells observed |
| EXP. 2 | Sic.Tox.2 + Sic.Enz.1 | All breast cancer cells are killed |
| EXP. 3 | Sic.Tox.3 + Sic.Enz.1 | No effect on the cells observed |
| EXP. 4 | Sic.Tox.4 + Sic.Enz.1 | No effect on the cells observed |
| EXP. 5 | Sic.Tox.5 + Sic.Enz.1 | No effect on the cells observed |

*Loxosceles laeta*

In this case a peptide toxin from the whole poison cocktail of about 95 kDa and as the phospholipase the enzyme fraction of *Loxosceles laeta* which elutes from the column after about 37–40 ml were specifically employed for large cell lung ca cells.

TABLE 17

Large cell lung ca with fractions from the poison of *Loxosceles laeta*

| Experiment No. | Substance combination | Result |
|---|---|---|
| EXP. 1 | Lox.Tox.1 + Lox.Enz.2 | No effect on the cells observed |
| EXP. 2 | Lox.Tox.2 + Lox.Enz.2 | No effect on the cells observed |
| EXP. 3 | Lox.Tox.3 + Lox.Enz.2 | No effect on the cells observed |
| EXP. 4 | Lox.Tox.4 + Lox.Enz.2 | No effect on the cells observed |
| EXP. 5 | Lox.Tox.5 + Lox.Enz.2 | No effect on the cells observed |
| EXP. 6 | Lox.Tox.6 + Lox.Enz.2 | No effect on the cells observed |
| EXP. 7 | Lox.Tox.7 + Lox.Enz.2 | All lung ca cells were destroyed<br>The normal lung tissue cells may be further cultivated |
| EXP. 8 | Lox.Tox.8 + Lox.Enz.2 | No effect on the cells observed |

Example 6

Synergistic and Time-Staggered Antagonistic Effect of Sic.Enz.2 on Sic.Tox.5

As described above, Sic.Enz.2 is selective for mamma ca cells (see substance combination 1 and Tab. 4). On the other hand, Sic.Enz.2 has also been described as blocking Sic.Tox.5 (see Tab. 13). Table 4 and Table 13, however, are based on two completely different experiments:

Table 4 describes the combination with respect to the selective killing of tumor cells in vitro. In this case, Sic.Enz.2 finds the malignant breast cancer cells, loosens the cell wall and makes it accessible for the peptide toxin so that Sic.Tox.5 may infiltrate and destroy the cell. For this purpose, the two substances are mixed immediately prior to their addition to the cell culture.

Although Table 13 describes the same combination of substances used, those were mixed with a time interval of 12 hours (first Sic.Enz.2, then Sic.Tox.5).

The results of these experiments are not contradictory since the combination according to experiment 5, Table 4 cannot be compared to the time-staggered enzyme/peptide blocking assay according to Table 8 as described herein. Under the conditions used in the enzyme/peptide blocking assay Sic.Enz.2 obviously also has an antagonistic effect on Sic.Tox.5.

Example 7

Further Experiments with Respect to the Antagonistic Effect

Generally spoken, the hyaluronidases and phospholipases each are a group/family of enzymes (Cantore G., Bettini S. (1958): Contributo allo studio dell azione farmocologica dell veneno di L. tredecimguttatus Rossi. Il Azione sulla musculatura bronchiale. Riv. parasit. 19:297) within which the individual members have different modes of action with respect to the nature of the substances to be degraded.

Up to now, these hyaluronidases and phospholipases have been described as penetration enzymes (Heitz J., Norment B. (1974): Characteristics of an alcaline phosphatase activity in brown recluse venom. Toxicon 12:181/Bernheimer A., et al. (1985): Comparative toxicology of *Loxosceles reclusa* and *Corynebacterium pseudotuberculosis*. Science 228:590–591).

In the frame of this invention it has been found that individual members of these enzyme groups used have an antagonistic effect on the peptide toxins employed thus limiting the temporal and spatial distribution of the peptide toxins.

Evidence for the antagonistic effect was achieved via the determination of the molecular weight of the substances used in a pre/post comparison by means of the electrophoreses already described by us. In the case of an antagonistic effect the initially present band of the peptide toxin is missing.

An experiment using a mixed cell culture of mamma ca and normal breast tissue cells after targeted addition of Sic.Tox.1 by means of a fine syringe into marked mamma ca cell rich areas revealed the following:

Sic.Tox.1 spreads relatively uniform for about 10 hours from the injection area in a circular direction. During this spreading both the normal and the tumorous cells are lysed. This process can be easily observed by means of an inverted microscope. After these 10 hours the distribution rate of Sic.Tox.1 is markedly slowed down while the specific cell destructive effect of Sic.Tox.1 could still be observed in intervals of 1, 2, and 7 days in the inverted microscope because at this time the area of cell destruction still became larger.

As already presented in Tables 13 and 14 Sic.Tox.1 was combined with 6 different Sic.enzymes. It was seen that upon addition of Sic.Enz.3 the cell lysing effect of Sic.Tox.1 was completely stopped after 9 hours. Electrophoresis of the medium and of a cell lysate showed no band at 72 kDa (molecular weight of Sic.Tox.1).

Using a modified Ouchterlony test an "antigen/antibody effect" of Sic.Enz.3 with respect to Sic.Tox.1 could also be demonstrated, i.e. binding of Sic.Enz.3 to Sic.Tox.1. In addition, it was observed that upon neutralization of Sic-.Tox.1 by Sic.Enz.3 the lysed areas were again overgrown.

The invention claimed is:

1. A pharmaceutical composition for the treatment of tumor diseases comprising in a pharmaceutically effective amount:

a) at least one peptide toxin derived from the venom of spiders of the family of Sicariidae having a molecular weight range of about 75 to 175 kDa, as well as b) at least one enzyme selected from the group consisting of phospholipases and hyaluronidases.

2. A pharmaceutical composition according to claim 1 further comprising at least one additional enzyme selected from the group consisting of phospholipases and hyaluronidases from the venom of spiders of the family of Sicariidae.

3. A pharmaceutical composition according to claim 1 in which at least one peptide toxin and at least one enzyme are derived from the venom of *Sicarius, Loxosceles, Scytodes*, and/or *Drymusa* spider species.

4. A pharmaceutical composition according to claim 3, in which the *Sicarius* spider species are selected from the group consisting of *Sicarius oweni, Sicarius testaceus, Sicarius hahni*, and *Sicarius albospinosus*, the *Loxosceles* spider species are selected from the group consisting *Loxosceles rufescens, Loxosceles reclusa*, and *Loxosceles laeta*, and the *Scytodes* spider species are selected from the group consisting of *Scytodes thoracica, Scytodes rufa*, and *Scytodes longipes.*

5. A pharmaceutical composition according to claim 1, in which at least one enzyme is derived from an organism different from spiders of the family of Sicariidae.

6. A pharmaceutical composition according to claim 1, in which the composition comprises at least one snake venom, preferably the pit viper venom captopril.

7. A pharmaceutical composition according to claim 1, in which at least one enzyme comprises at least one hyaluronidase from snake venoms, preferably from cobra venoms, or at least one phospholipase from *Actrataspis bibronji, Bitis arietans* or *Vipera aspis zinnikeri.*

8. A pharmaceutical composition according to claim 1, in which at least one enzyme is a phospholipase.

9. A pharmaceutical composition according to claim 1, in which at least one peptide toxin and at least one enzyme are obtained from the spider venom by a fractionation procedure.

10. A pharmaceutical composition according to claim 9, in which at least one peptide toxin and at least one enzyme are obtained from the spider venom by means of gel chromatography, HPLC, affinity chromatography and/or ion exchange chromatography.

11. A pharmaceutical composition according to claim 1, in which at least one peptide toxin and at least one enzyme have been obtained as follows:

obtaining a column with an inner diameter of 1.5 cm and a height of 50 cm tapering at the bottom to 1.5 mm, and which was filled with 20 mL of a gel chromatography gel AcA 34, matrix: 3% acrylamide/4% agarose, fractionation range: 20 to 350 Da, cut off limit: 750 kDa, bead diameter: 60–140 um;

loading spider venom from *Sicarius oweni, Sicarius testaceus, Sicarius hahni*, or *Sicarius albospinosus* in 0.25 M Tris/HC1, pH 6.5 to 7.3, and 1 .92 M glycine in distilled, deionized water onto the gel in a homogeneous form, passing the venom solution through the gel loading 165 mL of a solution of 0.25 M Tris/HC1, pH 6.5 to 7.3, and 1 .92 M glycine in distilled, deionized water onto the column, discarding the first 15 ml of the eluent ; and collecting fractions of 4 ml each, wherein the peptide toxins are found in fractions 1, 2, 4, 7, 9, and 10 and enzymes are found in fractions 3, 5, 6, 8, 11, and 12.

12. A pharmaceutical composition according to claim 1, in which at least one peptide toxin and at least one enzyme are derived from different fractions of the spider venom.

13. A pharmaceutical composition according to claim 1, in which at least one peptide toxin and at least one enzyme are present in an amount sufficient to produce a destructive effect with respect to tumor cells.

14. A pharmaceutical composition according to claim 13, in which the amount of at least one enzyme is selected to ensure a spatially and/or temporally controlled distribution of at least one peptide toxin within the tissue.

15. A pharmaceutical composition according to claim 1, further comprising carriers and/or excipients and/or further active agents.

16. A pharmaceutical composition according to claim 15, in which said carriers and/or excipients are isotonic solutions, preferably Ringer's solution, protein solutions, amino acid solutions, biocidal solutions, human albumin solution, and/or glutamine solution, and in which said further active agents are antibiotics, antimycotics, antituberculosis agents, anti-parasite agents, amino acids, enzymes promoting wound-healing, mitosis inhibitors and/or cytostatics.

17. A method for the preparation of a pharmaceutical composition comprising at least one peptide toxin as well as at least one enzyme selected from the group consisting of phospholipases and hyaluronidases wherein at least one peptide toxin is derived from the venom of spiders of the family of Sicariidae said method comprising:
   a) obtaining a spider venom,
   b) fractionating the mixture to obtain at least one peptide toxin,
   c) combining at least one peptide toxin obtained in step b) above with at least one enzyme selected from the group consisting of phospholipases and hyaluronidases to obtain a pharmaceutical composition.

18. A method according to claim 17, in which the spider venom is obtained from female spiders of the family of Sicariidae.

19. A method according to claim 17, in which the spider venom is obtained by manual milking.

20. A method according to claim 17, in which the spider venom is homogenized prior to fractionation.

21. A method according to claim 17, in which prior to further processing into a pharmaceutical composition the fractions are deep-frozen and further preferably lyophilized.

22. A method of treatment of tumor diseases comprising administering the pharmaceutical composition according to claim 1 to a patient in need thereof.

* * * * *